United States Patent [19]
Feldman

[11] Patent Number: 5,902,292
[45] Date of Patent: *May 11, 1999

[54] EYE DROP APPLICATOR

[76] Inventor: Edward L. Feldman, 232 Cedar Park Cir., Sarasota, Fla. 34242

[*] Notice: This patent is subject to a terminal disclaimer.

[21] Appl. No.: 08/973,620

[22] PCT Filed: Jun. 7, 1996

[86] PCT No.: PCT/US96/10111

§ 371 Date: Dec. 5, 1997

§ 102(e) Date: Dec. 5, 1997

[87] PCT Pub. No.: WO96/40025

PCT Pub. Date: Dec. 19, 1996

Related U.S. Application Data

[63] Continuation-in-part of application No. 08/478,724, Jun. 7, 1995, Pat. No. 5,578,019.

[51] Int. Cl.⁶ .................................................. A61M 35/00
[52] U.S. Cl. ........................................ 604/295; 600/300
[58] Field of Search ..................................... 604/295, 298, 604/300, 301, 302; 220/254, 253, 252, 715; 222/420, 421; 215/228, 237, 238, 311

[56] References Cited

U.S. PATENT DOCUMENTS

| | | | |
|---|---|---|---|
| 3,058,466 | 10/1962 | Routsong | 128/233 |
| 3,279,466 | 10/1966 | Mings | 128/233 |
| 3,598,121 | 8/1971 | Lelicoff | 128/233 |
| 3,872,866 | 3/1975 | Lelicoff | 128/233 |
| 4,002,168 | 1/1977 | Petterson | 128/233 |
| 4,085,750 | 4/1978 | Bosshold | 128/233 |
| 4,543,096 | 9/1985 | Keene | 604/300 |
| 4,605,398 | 8/1986 | Herrick | 604/300 |
| 4,834,727 | 5/1989 | Cope | 604/300 |
| 4,973,322 | 11/1990 | Jewart | 604/300 |
| 5,064,420 | 11/1991 | Clarke et al. | 604/295 |
| 5,154,710 | 10/1992 | Williams | 604/301 |
| 5,207,657 | 5/1993 | Gilbilisco | 604/295 |
| 5,295,981 | 3/1994 | Smith et al. | 604/301 |
| 5,366,448 | 11/1994 | Basilice et al. | 604/300 |
| 5,578,019 | 11/1996 | Feldman | 604/300 |

*Primary Examiner*—John G. Weiss
*Assistant Examiner*—David J. Cho
*Attorney, Agent, or Firm*—Oppedahl & Larson LLP

[57] ABSTRACT

A bottle for administering liquid eye drops, comprising:

(a) a container (10) for holding the liquid eye drops;

(b) a dispensing assembly (11, 61), and (c) a closure assembly (12, 63). The dispensing assembly is coupled to the container and has a passage (13, 62) therethrough for dispensing of the liquid eye drops from the container. The closure assembly (12, 63) is pivotally mounted on the dispensing assembly (11, 61) and moves between a closed or storage position in which the passage (13, 62) in the dispensing assembly (11, 61) is sealed by a closure seat (32, 65) disposed on the interior surface of the closure assembly, and an open position in which the passage is open for dispensing eye drops. An eye lid retractor (14, 66) is attached to the exterior surface of the closure assembly for retracting the lower eye lid of an individual to whom the eye drops are being administered. The dispensing assembly and the closure assembly may also be provided as a separate cap unit for attachment to a conventional eye drop bottle, and such a cap is a further aspect of the present invention.

7 Claims, 4 Drawing Sheets

EYE DROP APPLICATOR

This application is a continuation-in-part of U.S. patent application Ser. No. 08/478,724 filed Jun. 7, 1995, now U.S. Pat. No. 5,578,019.

BACKGROUND OF THE INVENTION

This application relates to an improved bottle for dispensing liquid eye drops.

Liquid eye drops are commonly used to introduce over-the-counter and prescription medications into the eyes of human patients. The most common container in which these eye drops are supplied is simply a bottle with a tapered dropper. Notwithstanding the ubiquitous nature of such containers, it has been recognized that a container with a tapered nozzle does not provide for optimum means for administering drops into the eye. In fact, people using such bottles frequently bring their fingers into contact with their eye and eye lids to hold the eye open for administration of the eye drops which increases the risk of eye infection. In addition, traditional elongated eye dropper bottle tips may come in contact with eye secretions increasing the risk of contamination. Furthermore, the tendency of many persons to blink or flinch away during the application of the eye drops makes the administration of a consistent dosage of eye drops difficult for many.

Many different styles of eye drop bottles have been proposed to overcome the difficulties of the standard eye drop bottle. For example, U.S. Pat. Nos. 3,058,466; 3,279,466; 3,598,121; 3,872,866; 4,085,750; 4,543,096; 4,605,398; 4,834,727; 4,973,322; 5,064,420; 5,154,710 and 5,295,981, which are incorporated herein by reference, each disclose removable attachments which are affixed to a conventional dropper bottle. None of these devices have found commercial acceptance, however, perhaps because they all are complicated designs involving several separable parts and removable lids. U.S. Pat. No. 4,002,168, which is incorporated herein by reference, discloses a variety of different designs for an eye drop applicator which incorporate eye lid retractors of various types. In one embodiment, the eye lid retractor is pivotally moveable with respect to the dispensing orifice, and is said to achieve sealing of the orifice when pivoted into a closed position. No structure for accomplishing this sealing is disclosed, however.

It is an object of the present invention to provide an improved design for an eye drop applicator with an eye lid retractor, and in particular to provide a design for an eye drop applicator in which no separation or assembly of pieces is necessary to use or store the applicator.

SUMMARY OF THE INVENTION

In accordance with the present invention, there is provided a bottle for administering liquid eye drops, comprising:

(a) a container for holding the liquid eye drops;

(b) a dispensing assembly, said dispensing assembly being coupled to the container and having a passage therethrough for dispensing of the liquid eye drops from the container; and (c) a closure assembly comprising a base portion having means for sealing the passage in the dispensing assembly disposed on an interior surface thereof and means for retracting the lower eye lid of an individual to whom the eye drops are being administered disposed on the exterior surface thereof. The closure assembly is pivotally mounted on the dispensing assembly to permit movement of the closure assembly between a first position in which the passage in the dispensing assembly is sealed by the means for sealing the passage in the dispensing assembly and a second position in which the passage in the dispensing assembly is open to permit dispensing of the liquid eye drops. A locking mechanism is provided such that the closure assembly is fixed in the second position when pressure sufficient to retract an eyelid is applied. The dispensing assembly and the closure assembly may also be provided as a separate unit for attachment to a conventional eye drop bottle, and such a cap is a further aspect of the present invention.

DETAILED DESCRIPTION OF THE INVENTION

Figure 1A:
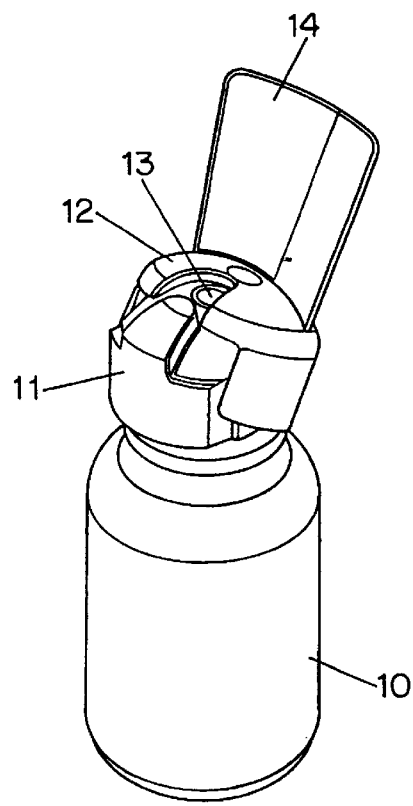
FIGS. 1A and 1B show an embodiment of an eye drop bottle in accordance with the invention with the closure assembly in the open and closed positions, respectively.
Figure 1B:
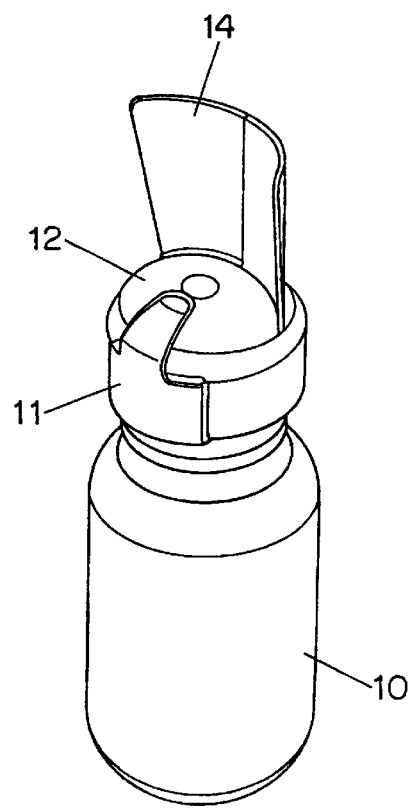

The present invention provides an eye drop applicator with an easy to use eye lid retractor which is incorporated as part of the cap of the applicator. As shown in FIGS. 1A and 1B, a first embodiment of the eye drop bottle of the invention comprises a container 10, a dispensing assembly 11 and a closure assembly 12. The dispensing assembly 11 is coupled to the container 10 and has a passage 13 extending therethrough for dispensing liquid eye drops from the container. The closure assembly 12 is pivotally mounted on the dispensing assembly 11 and is moveable between an open position, shown in FIG. 1A and a closed position shown in FIG. 1B.

In the open position, the closure assembly 12 is pivoted away from the axis of the container as a whole, exposing the end of passage 13 and permitting the dispensing of eye drops. In addition, a blade-like eye lid retractor 14 is disposed in a position for effective application of eye drops when the eye lid retractor 14 is placed against the lower lid area of a user, i.e., the lid retractor is angled for correct drop placement. The exact angle necessary to achieve this result will depend on the length of the retractor 14 and the lateral separation between the passage 13 and the retractor 14. In the closed position (FIG. 1B), the closure assembly 12 covers the open end of the passage 13 and seals the applicator for storage.

Figure 2A:
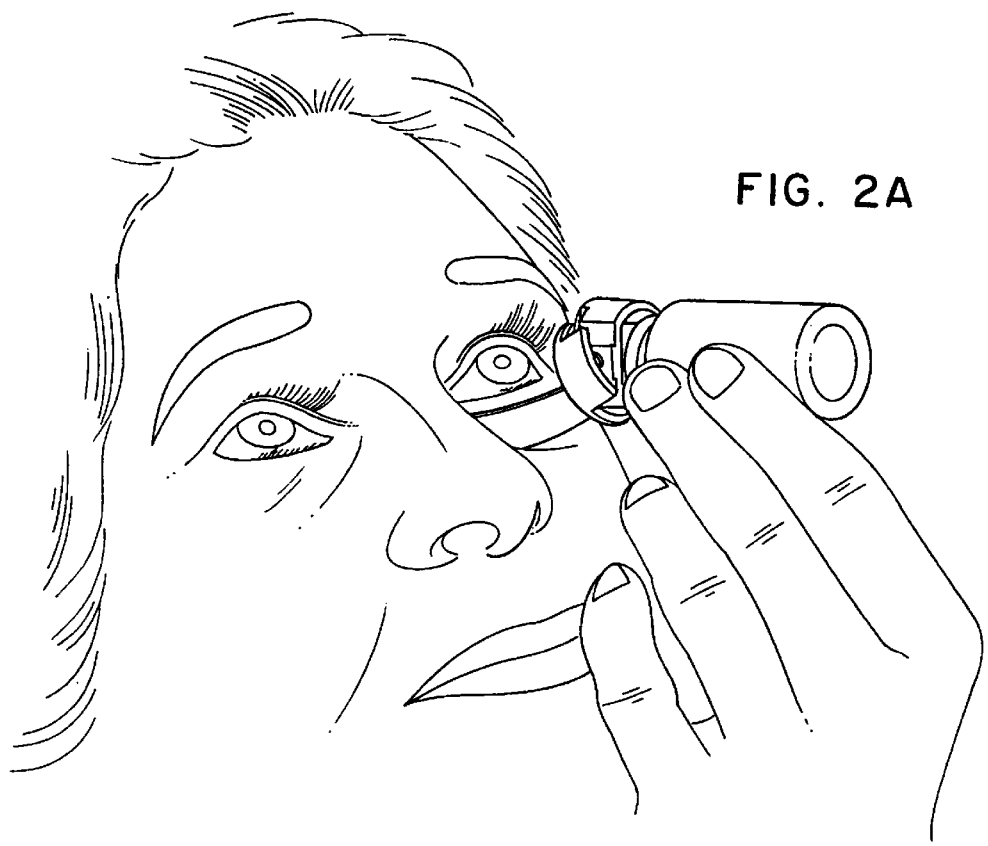
FIG. 2 shows an individual using an eye drop applicator in accordance with the invention.
Figure 2B:
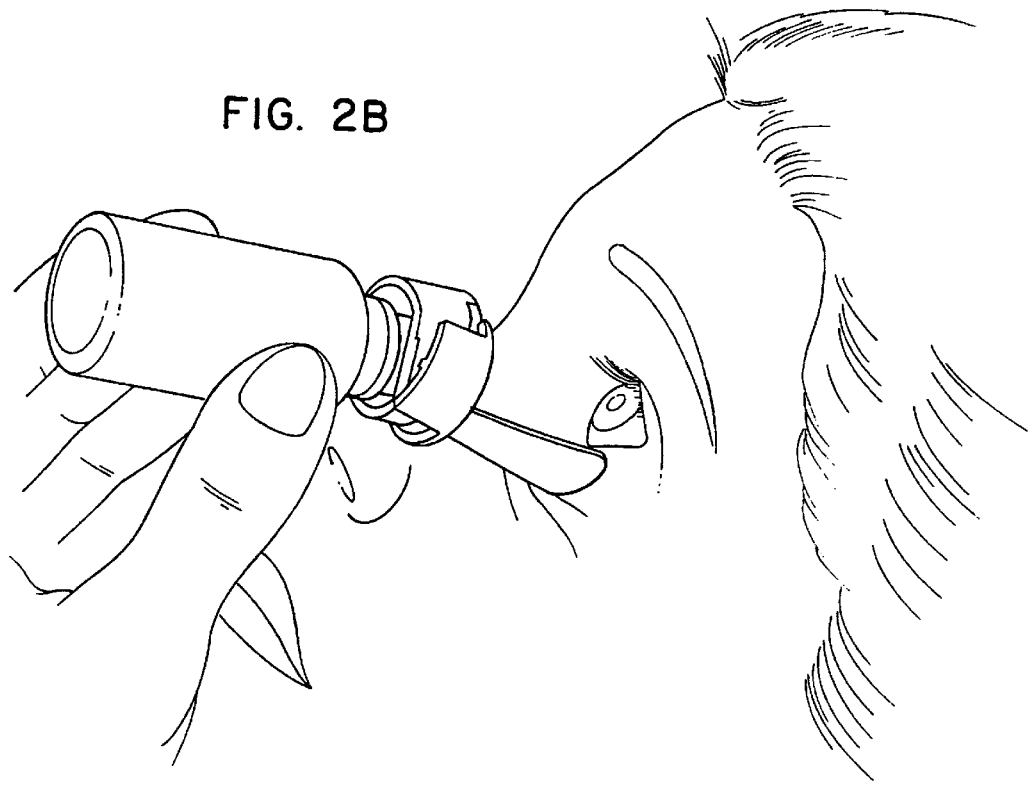

FIGS. 2A and 2B shows the manner in which an applicator in accordance with the invention is used. As shown, the user tips his or her head slightly backwards, and places the eye lid retractor 14 against the lower lid 21 with the closure assembly in the open position. This everts the lower eye lid away from the eye, opening the cul-de-sac between the lower lid ands the globe of the eye, and brings the opening of the passage 13 into a proper position relative to the eye so that when drops are dispensed from the applicator they will enter the eye. Dispensing of drops can then be accomplished by squeezing the container 10. The retractor can also be used to apply pressure to the lower lid after drop application to limit the entry of eye drops into the tear drainage system.

Figure 3A:
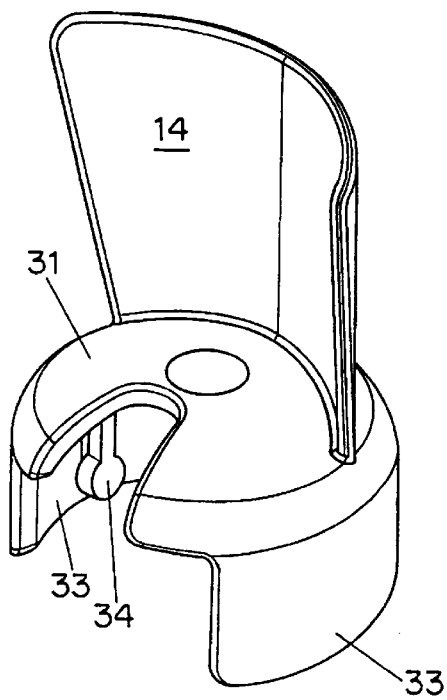
FIGS. 3A and 3B shows a closure assembly in accordance with the invention.
Figure 3B:
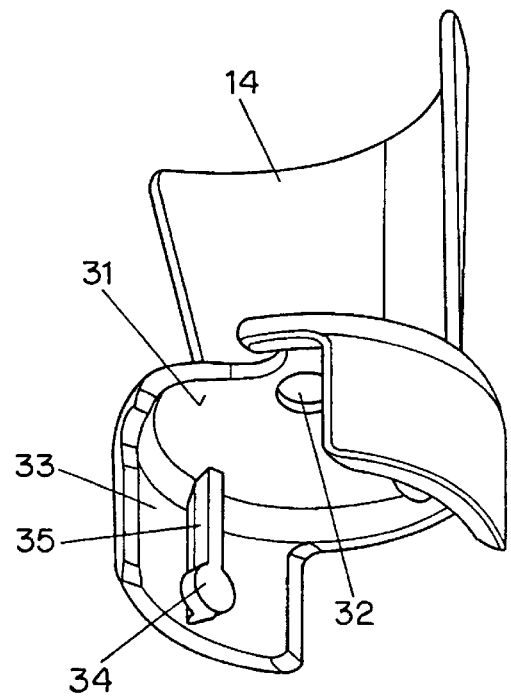

FIGS. 3A and 3B are top and bottom perspective views showing the closure assembly of the first embodiment of the invention in greater detail. As shown, the closure assembly has a base portion formed from a substantially circular and domed top portion and two skirts 33. An eye lid retractor 14 is attached to the exterior surface of the top portion 31. A notch is taken out of the top portion 31 extending from the edge of the top portion to a point just short of the center. In the center of the underside of the top portion is a closure seat 32 which acts to engage and seal the opening of the passage 13 through the dispensing assembly 11 when the closure assembly is in the closed or storage position.

The closure seat 32 may be a flexible and compressible material which is affixed to interior surface of the top portion. Preferred materials for this purpose are synthetic rubbers, elastomers, and photopolymerizable resins useful in implementing computer-assisted-designs. Alternatively, the closure seat may be a defined region on the interior surface of top portion which interacts with a flexible and compressible material on the dispensing assembly to seal the passage through the dispensing assembly.

The two opposed skirts 33 extend downward from the edges of the top portion 31 and are symmetrically disposed on either side of the base portion with respect to the eye lid retractor, leaving the edges of the top portion along the front and the back of the base portion free. Bearing members 34 are disposed on the interior surface of each skirt for pivoting articulation with a bearing seat 46 on the dispensing assembly (See FIG. 4). The bearing member 34 may also include a detent 35 for fixing the closure assembly in the open and closed position.

The eye lid retractor 14 is shown as a spatulate member which is curved to conform to the average curvature of the human lower lid area. It will be understood, however, that other designs for the eye lid retractor, including open loop designs, could be employed.

Figure 4:
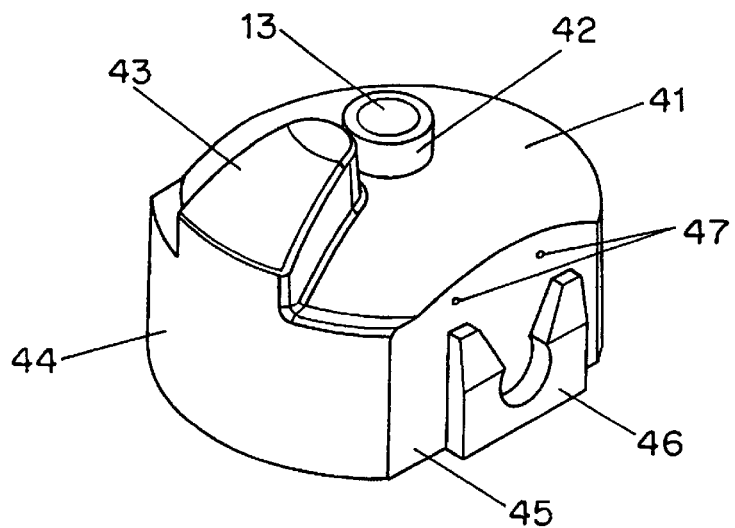
FIG. 4 shows an exterior view of a dispensing assembly in accordance with the invention.

FIG. 4 shows an top perspective view of a dispensing assembly in accordance with the invention. The dispensing assembly has a substantially circular top 41 on which is disposed a dispensing nozzle 42 surrounding the end of passage 13 which extends through the dispensing assembly, and a dirt seal 43.

The dispensing nozzle 42 engages with the closure seat 32 of the closure assembly to seal the passage 13 when the closure assembly is in the closed or storage position. Advantageously, the dispensing nozzle 42 will have a soft compressible sealing ring affixed to the end thereof for this purpose.

The dirt seal 43 extends upwards from the top portion 41 of the dispensing assembly and is sized to fit within the notch in the top 31 of the closure assembly. The purpose of the dirt seal 43 is to prevent contamination of the dispensing nozzle 42 when the applicator is not in use. The dirt seal 43 and the top portion 12 may snap together using a detent to fix the applicator in a closed position for storage.

Extending downward from the top 41 of the dispensing assembly is a skirt 44. The skirt 44 has two opposed surfaces 45 which are flattened and on which the bearing seats 46 and optional detents 47 are disposed. Bearing members 34 snap into bearing seats 46 which permit pivoting movement of the closure assembly between two defined positions, while holding the closure assembly to the dispensing assembly. Male and female detents 35 and 47 interact to fix the closure assembly into one of the two positions. Of course, it will be understood that the term "fix" in this case does not imply any degree of permanence, but only indicates the fact that the closure assembly is held in one of the two defined positions until some force is applied to move the closure assembly. In particular, the detent means should fix the closure assembly in the open position such that it will remain in this position when the eyelid retractor is pressed against an eyelid with sufficient force to evert the lower eyelid.

Figure 5:
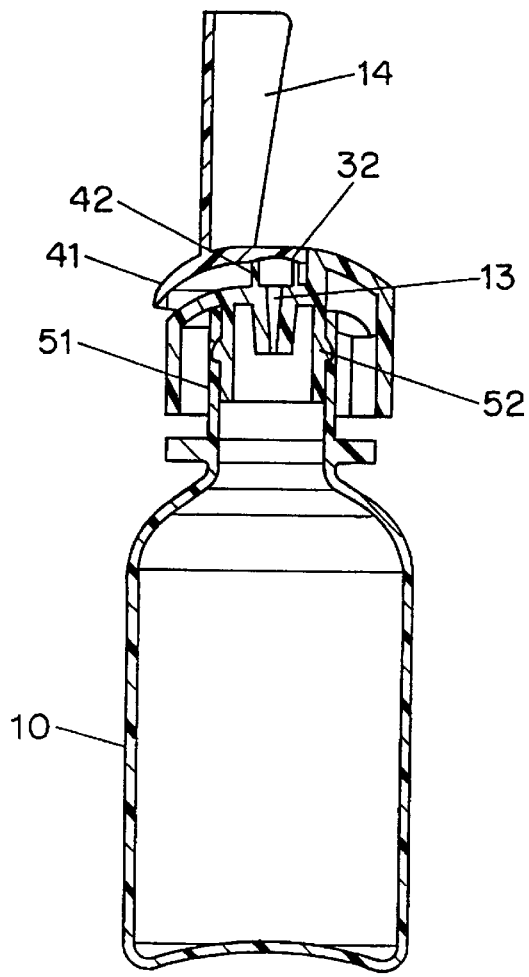
FIG. 5 shows a cross section of an applicator bottle in accordance with the invention.

FIG. 5 shows a cross-section of an applicator bottle in accordance with the invention in a plane which bisects the eye lid retractor 14 when the closure assembly is in the closed position. In this embodiment of the invention, the dispensing assembly is coupled to the neck 51 of the container 10 by a tightly fitting stopper portion 52. Alternative means for coupling the dispenser assembly to the container include threaded couplings and glued joints. In addition, the dispensing assembly may be formed as an integral part of the container.

FIG. 5 also shows the sealing interaction of the closure seat 32 and the dispensing nozzle 42 when the closure assembly is in the closed or storage position. As shown in FIG. 5, a flexible closure seat 42 is disposed on the interior surface of the top 41 of the closure assembly.

Figure 6A:
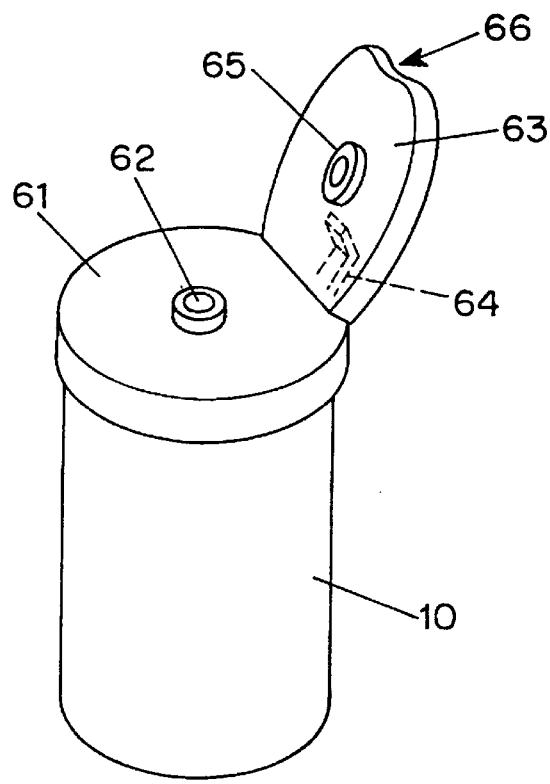
FIGS. 6A–6D show a second embodiment of an eye drop applicator in accordance with the invention.
Figure 6B:
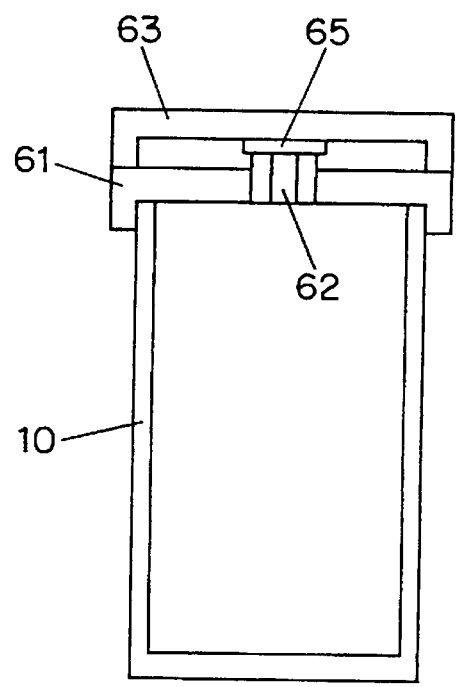
Figure 6C:
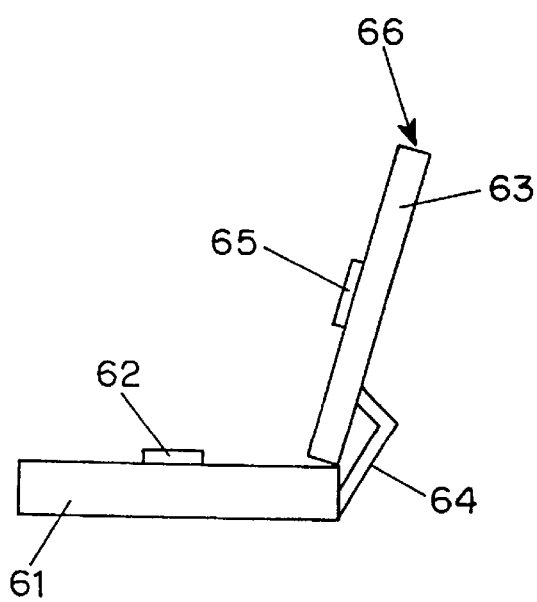

FIGS. 6A–6D show a second embodiment of the applicator bottle of the invention. As shown, dispensing assembly 61 is affixed to bottle 10, for example using a threaded or snap-on coupling. Dispensing assembly 61 has a passage 62 therein for dispensing of eye drops from the bottle. A closure assembly 63 is pivotably connected to dispensing assembly 61 by hinge 64. A flexible closure seat 65 is aligned to seal the passage 62 when the closure assembly is pivoted into a closed position as shown in cross-sectional view FIG. 6B. One edge 66 of the closure assembly 63 is cut back into a concave surface to match the curvature of a lower eyelid and serves as the retractor in this embodiment of the invention. FIG. 6C shows a side view of the dispensing and closure assembly of the second embodiment in the open position.

Figure 6D:
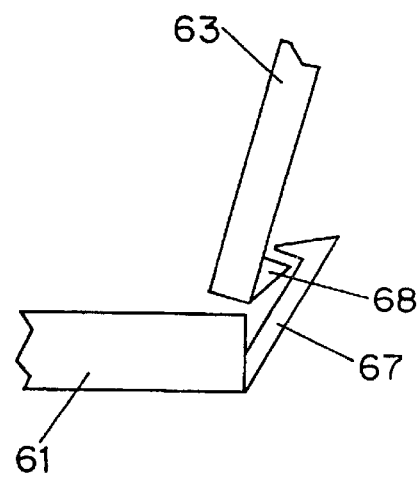

As in the case of the first embodiment, detents or latches can be used to fix the closure assembly in either the open or the closed position. For example, as shown in FIG. 6D a latch 67 can be affixed into the dispensing assembly 61 which interacts with a ridge 68 on the closure assembly 63 to hold closure assembly in the open position. Alternatively, a detent could be attached to a member extending from the dispensing assembly 61 and positioned within in a slot in the closure assembly 63.

While the foregoing discussion has been directed to a complete applicator bottle, it will be apparent to those skilled in the art that novel features of the present invention reside in the combination of the dispensing assembly and the closure assembly, and that such a cap combining these two assemblies could be advantageously placed on a conventional eye drop bottle provided that a compatible coupling means were included. Thus, a further aspect of the invention is a cap for an eye drop bottle. The cap comprises a dispensing assembly which includes means for coupling the dispensing assembly to a container for holding eye drops and having a passage therethrough for dispensing of the liquid eye drops from the container. Suitable means for coupling the dispensing assembly to the bottle will depend on the nature of the bottle but will generally be a threaded channel compatible with the threads of the bottle or a stopper. The cap of the invention further comprises a closure assembly. As in the case of the complete bottle of the invention, the closure assembly has means for sealing the passage in the dispensing assembly and means for retracting the lower eye lid of an individual to whom the eye drops are being administered, wherein said closure assembly is pivotally mounted on the dispensing assembly to permit movement of the closure assembly between a first position in which the passage in the dispensing assembly is sealed by the means for sealing the passage in the dispensing assembly and a second position in which the passage in the dispensing assembly is open to permit dispensing of the liquid eye drops.

The applicator bottle and the cap of the invention are advantageously made from plastics such as polyethylene, polypropylene, polyester or photopolymerizable resins suitable for implementing and constructing computer-assisted designs, and may be made from a combination of materials.

As will be apparent from the foregoing description, the present invention offers many advantages over previously known eye drop applicators. In particular, the present invention permits the facile application of drops without having to contact the eye with the fingers, from an applicator which requires no separation of parts to use. Further, the applicator of the invention can be used with one hand.

A further advantage of the invention is the tactile feedback provided by contacting the retractor to the lower lid. This makes it possible for persons with poor vision or poor fine motor control to correctly position the applicator for dispensing drops. The spacing between the eye and the tip that results from the use of the retractor also limits the likelihood of contact with the eye, which could result in injury to the eye or in contamination of the liquid eye drops in the container.

I claim:

1. A cap for an eye drop bottle comprising,
   (a) a dispensing assembly, said dispensing assembly comprising means for coupling the dispensing assembly to a container for holding eye drops and having a passage therethrough for dispensing of the liquid eye drops from the container;
   (b) a closure assembly comprising a base portion having means for sealing the passage in the dispensing assembly disposed on an interior surface thereof and means for retracting the lower eye lid of an individual to whom the eye drops are being administered disposed on an exterior surface thereof, wherein said closure assembly is pivotally mounted on the dispensing assembly to permit movement of the closure assembly between a first position in which the passage in the dispensing assembly is sealed by the means for sealing the passage in the dispensing assembly and a second position in which the passage in the dispensing assembly is open to permit dispensing of the liquid eye drops; and
   (c) means for fixing the closure assembly in the second position, thereby holding the closure assembly in the second position when the means for retracting the lower eye lid is pressed against an eye lid with sufficient force to retract the eyelid.

2. A cap according to claim 1, wherein the means for fixing the closure assembly in the second position are male and female locking detents.

3. A cap according to claim 1, further comprising means for fixing the closure assembly in the first and second positions.

4. A cap according to claim 1, wherein the means for sealing the passage is a flexible and compressible member affixed on the interior surface of the base portion of the closure assembly.

5. A cap according to claim 1, wherein the closure assembly is a disc-shaped member having a substantially circular edge, said closure assembly being pivotably connected to the dispensing assembly at a first location on the edge and having a curved concave cut back along the edge at a second location opposite to the first location, said cut back matching the curvature of a lower eyelid.

6. A bottle for administration of liquid eye drops comprising a container for holding liquid eye drops and a cap affixed to the container, said cap comprising:
   (a) a dispensing assembly (11, 61), said dispensing assembly comprising means (52) for coupling the dispensing assembly to a container (10) for holding eye drops and having a passage (13, 62) therethrough for dispensing of the liquid eye drops from the container (10);
   (b) a closure assembly (12, 63) comprising a base portion (31, 63) having means (32, 65) for sealing the passage in the dispensing assembly disposed on an interior surface thereof and means (14, 66) for retracting the lower eye lid of an individual to whom the eye drops are being administered disposed on an exterior surface thereof, wherein said closure assembly (12, 63) is pivotally mounted on the dispensing assembly (11, 61) to permit movement of the closure assembly (12, 63) between a first position in which the passage (13, 62) in the dispensing assembly is sealed by the means (32, 65) for sealing the passage in the dispensing assembly and a second position in which the passage (12, 63) in the dispensing assembly is open to permit dispensing of the liquid eye drops; and
   (c) means (35, 47; 67, 68) for fixing the closure assembly (12, 63) in the second position, thereby holding the closure assembly in the second position when the means (14, 66) for retracting the lower eye lid is pressed against an eye lid with sufficient force to retract the eyelid.

7. A bottle according to claim 6, wherein the closure assembly is a disc-shaped member having a substantially circular edge, said closure assembly being pivotably connected to the dispensing assembly at a first location on the edge and having a curved concave cut back along the edge at a second location opposite to the first location, said cut back matching the curvature of a lower eyelid.

* * * * *